US012805718B2

(12) United States Patent
Li

(10) Patent No.: US 12,805,718 B2
(45) Date of Patent: Nov. 24, 2026

(54) OCT SIGNAL PROCESSING METHOD, OCT DEVICE, AND PROGRAM

(71) Applicant: NIKON CORPORATION, Tokyo (JP)

(72) Inventor: Yongbo Li, Ebina (JP)

(73) Assignee: NIKON CORPORATION, Tokyo (JP)

(*) Notice: Subject to any disclaimer, the term of this patent is extended or adjusted under 35 U.S.C. 154(b) by 274 days.

(21) Appl. No.: 18/573,035

(22) PCT Filed: Jun. 24, 2021

(86) PCT No.: PCT/JP2021/024001
§ 371 (c)(1),
(2) Date: Dec. 21, 2023

(87) PCT Pub. No.: WO2022/269876
PCT Pub. Date: Dec. 29, 2022

(65) Prior Publication Data
US 2024/0293023 A1 Sep. 5, 2024

(51) Int. Cl.
*A61B 3/10* (2006.01)

(52) U.S. Cl.
CPC .................................... *A61B 3/102* (2013.01)

(58) Field of Classification Search
CPC .............................. A61B 3/102; A61B 3/0025
See application file for complete search history.

(56) References Cited

U.S. PATENT DOCUMENTS 9,109,870 B2 8/2015 Bajraszewski et al.
2018/0028056 A1* 2/2018 Kubota ..................... G06T 7/12
2018/0084991 A1 3/2018 Shibutani et al.
2018/0153395 A1* 6/2018 Goto .................. G01B 9/02091
2018/0360306 A1* 12/2018 Kulkarni .............. A61B 3/0033

FOREIGN PATENT DOCUMENTS

JP 2012-024551 A 2/2012
JP 2018-015189 A 2/2018
JP 2018-047099 A 3/2018

OTHER PUBLICATIONS

Extended European Search Report issued in corresponding European Application No. 21947161.2 dated Feb. 21, 2025 (11 pages).

* cited by examiner

*Primary Examiner* — Sharrief I Broome
*Assistant Examiner* — K Muhammad
(74) *Attorney, Agent, or Firm* — Foley & Lardner LLP

(57) ABSTRACT

An OCT signal processing method of a processor performing processing on a detection signal obtained by separating light emitted from a light source into measurement light and reference light, guiding the measurement light to an eye to be examined using an object optical system, guiding the reference light to a reference optical system, followed by photo-detecting interference light resulting from measurement light reflected from the eye to be examined interfering with the reference light. The OCT signal processing method includes a step of generating an OCT signal by performing Fourier transformation on the detection signal, a step of detecting a peak portion in the OCT signal, and a step of generating a first corrected OCT signal by removing the peak portion from the OCT signal.

11 Claims, 14 Drawing Sheets

OCT SIGNAL PROCESSING METHOD, OCT DEVICE, AND PROGRAM

CROSS-REFERENCE TO RELATED APPLICATIONS

This application is a National Stage of International Application No. PCT/JP2021/024001, filed Jun. 24, 2021, the disclosure of which is incorporated herein by reference in its entirety.

TECHNICAL FIELD

Technology disclosed herein is related to an OCT signal processing method, an OCT device, and a program.

BACKGROUND ART

A device to generate a tomographic image of an eye to be examined is disclosed in U.S. Pat. No. 9,109,870. There is a desire to obtain a tomographic image with suppressed artifacts.

SUMMARY OF INVENTION

Technical Problem

An OCT signal processing method of a first aspect of technology disclosed herein includes a processor performing processing on a detection signal obtained by separating light emitted from a light source into measurement light and reference light, guiding the measurement light to an eye to be examined using an object optical system, guiding the reference light to a reference optical system, followed by photo-detecting interference light resulting from measurement light reflected from the eye to be examined interfering with the reference light. The OCT signal processing method includes a step of generating an OCT signal by performing Fourier transformation on the detection signal, a step of detecting a peak portion in the OCT signal, and a step of generating a first corrected OCT signal by removing the peak portion from the OCT signal.

An OCT device of a second aspect of technology disclosed herein is an OCT device including a processor. In the OCT device the processor performs processing on a detection signal obtained by separating light emitted from a light source into measurement light and reference light, guiding the measurement light to an eye to be examined using an object optical system, guiding the reference light to a reference optical system, followed by photo-detecting interference light resulting from measurement light reflected from the eye to be examined interfering with the reference light. The processor executes a step of generating an OCT signal by performing Fourier transformation on the detection signal, a step of detecting a peak portion in the OCT signal, and a step of generating a first corrected OCT signal by removing the peak portion.

A program of a third aspect of technology disclosed herein is a program that causes a computer to execute processing on a detection signal obtained by separating light emitted from a light source into measurement light and reference light, guiding the measurement light to an eye to be examined using an object optical system, guiding the reference light to a reference optical system, followed by photo-detecting interference light resulting from measurement light reflected from the eye to be examined interfering with the reference light. The program causes the computer to execute a step of generating an OCT signal by performing Fourier transformation on the detection signal, a step of detecting a peak portion in the OCT signal, and a step of generating a first corrected OCT signal by removing the peak portion.

DESCRIPTION OF EMBODIMENTS

Detailed explanation follows regarding exemplary embodiments of technology disclosed herein, with reference to the drawings.

Figure 1:
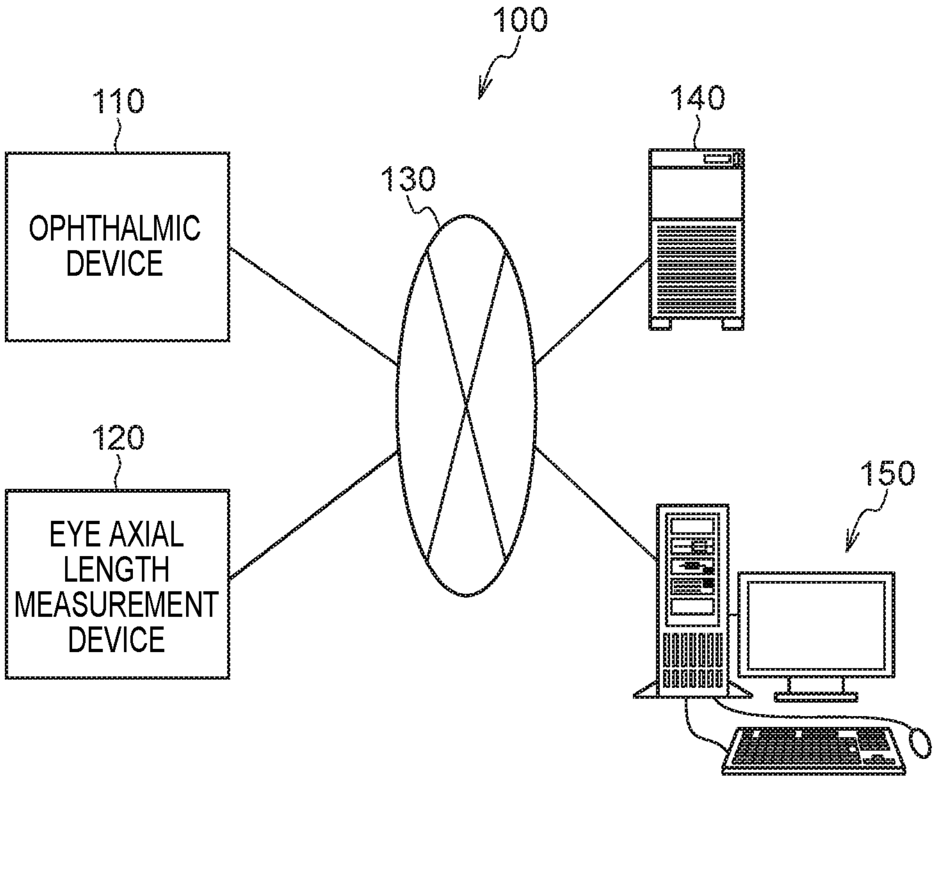
FIG. 1 is a block diagram illustrating a configuration of an ophthalmic system 100 of a first exemplary embodiment.

Explanation follows regarding a configuration of an ophthalmic system 100 of a first exemplary embodiment, with reference to FIG. 1. As illustrated in FIG. 1, the ophthalmic system 100 includes an ophthalmic device 110, an eye axial length measurement device 120, a management server device (referred to hereafter as "server") 140, and an image display device (referred to hereafter as "viewer") 150. The ophthalmic device 110 acquires an image of a fundus. The eye axial length measurement device 120 measures the axial length of the eye of a patient. The server 140 stores fundus images that were obtained by imaging the fundus of patients using the ophthalmic device 110 in association with patient IDs. The viewer 150 displays medical information such as fundus images acquired from the server 140.

The ophthalmic device 110, the eye axial length measurement device 120, the server 140, and the viewer 150 are connected together through a network 130. The network 130 is a freely selected network such as a LAN, WAN, the internet, a wide area Ethernet, or the like. For example, a LAN may be employed as the network 130 in cases in which the ophthalmic system 100 is built for a single hospital.

The viewer 150 is a client in a client-server system, and plural such devices are connected together through a network. There may also be plural devices for the server 140 connected through the network in order to provide system redundancy. Alternatively, if the ophthalmic device 110 is provided with image processing functionality and with the image viewing functionality of the viewer 150, then the fundus images may be acquired and image processing and image viewing performed with the ophthalmic device 110 in a standalone state In such cases the viewer 150 may be omitted. Moreover, if the server 140 is provided with the image viewing functionality of the viewer 150, then the fundus images may be acquired and image processing and image viewing performed by configuration of the ophthalmic device 110 and the server 140. In such cases the viewer 150 may be omitted.

Note that other ophthalmic equipment (examination equipment for measuring a field of view, measuring intraocular pressure, or the like) and/or a diagnostic support device that analyzes images using artificial intelligence (AI) may be connected to the ophthalmic device 110, the server 140, and the viewer 150 over the network 130.

Figure 2:
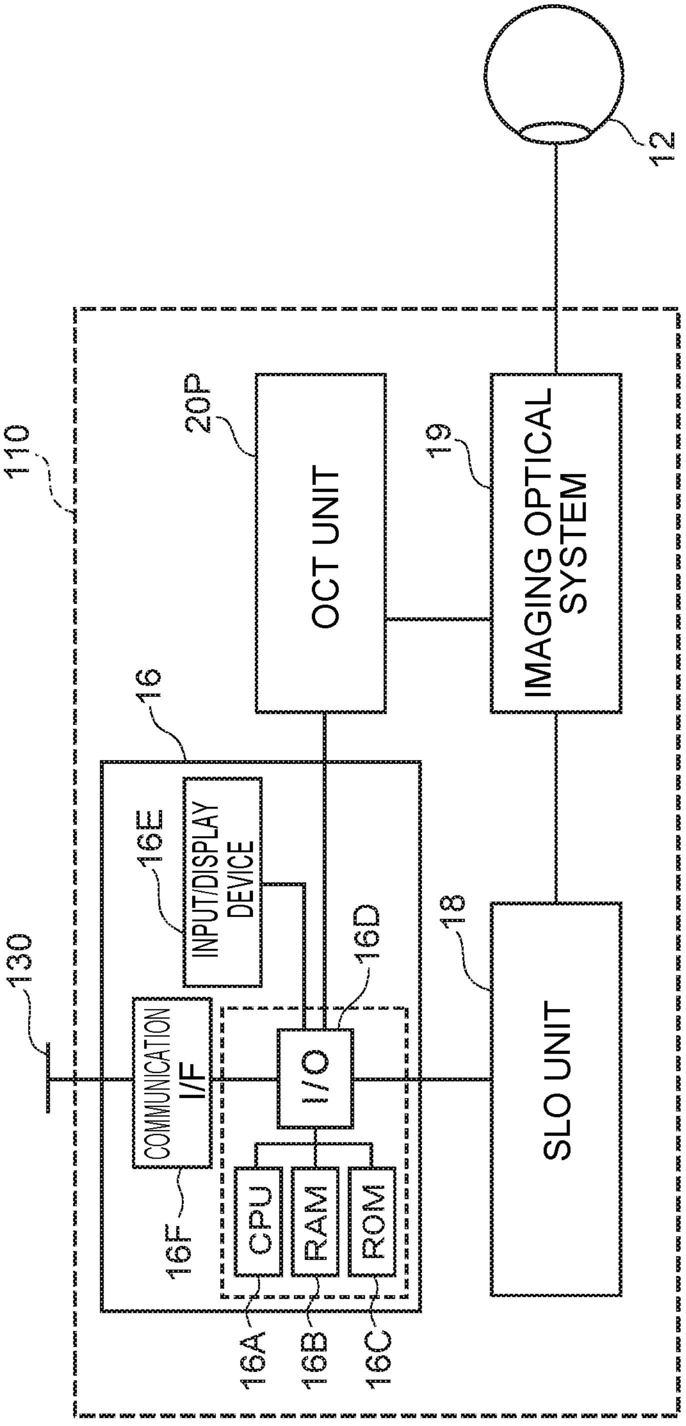
FIG. 2 is a block diagram illustrating a configuration of an ophthalmic device 110.

Next, explanation follows regarding a configuration of the ophthalmic device 110, with reference to FIG. 2.

For ease of explanation, scanning laser ophthalmoscope is abbreviated to SLO. Moreover, optical coherence tomography is abbreviated to OCT.

With the ophthalmic device 110 installed on a horizontal plane and a horizontal direction taken as an "X direction", a direction perpendicular to the horizontal plane is denoted a "Y direction", and a direction connecting the center of the pupil at the anterior eye portion of the eye to be examined 12 and the center of the eyeball is denoted a "Z direction". The X direction, the Y direction, and the Z direction are thus orthogonal to each other.

The ophthalmic device 110 includes an SLO unit 18, an OCT unit 20P, an imaging optical system 19, and a control device 16, and acquires a fundus image by imaging the fundus of the eye to be examined eye 12. Two-dimensional fundus images that have been acquired by the SLO unit 18 are referred to as SLO images. Tomographic images, face-on images (en-face images) and the like of the retina created based on OCT data acquired by the OCT unit 20P are referred to as OCT images.

The control device 16 includes a computer provided with a Central Processing Unit (CPU) 16A, Random Access Memory (RAM) 16B, Read-Only Memory (ROM) 16C, and an input/output (I/O) port 16D. A signal processing program, described later, is stored on the ROM 16C.

The CPU 16A is an example of a "processor" of technology disclosed herein. The signal processing program stored on the ROM 16C is an example of a "program" of technology disclosed herein.

The control device 16 includes an input/display device 16E connected to the CPU 16A through the I/O port 16D. The input/display device 16E includes a graphical user interface to display images of the eye to be examined 12 and to receive various instructions from a user. An example of the graphical user interface is a touch panel display.

The control device 16 generates images of the eye to be examined 12 based on data acquired by the imaging described above. The control device 16 includes a communication interface (I/F) 16F connected to the I/O port 16D. The ophthalmic device 110 is connected to the eye axial length measurement device 120, the server 140, and the viewer 150 through the communication interface (I/F) 16F and the network 130.

Although the control device 16 of the ophthalmic device 110 is provided with the input/display device 16E as illustrated in FIG. 2, the technology disclosed herein is not limited thereto. For example, a configuration may adopted in which the control device 16 of the ophthalmic device 110 is not provided with the input/display device 16E, and instead a separate input/display device is provided that is physically independent of the ophthalmic device 110. In such cases, the display device is provided with an image processing processor unit that operates under the control of the CPU 16A in the control device 16. Such an image processing processor unit may display SLO images and the like based on image signals instructed by output of the CPU 16A.

Figure 3A:
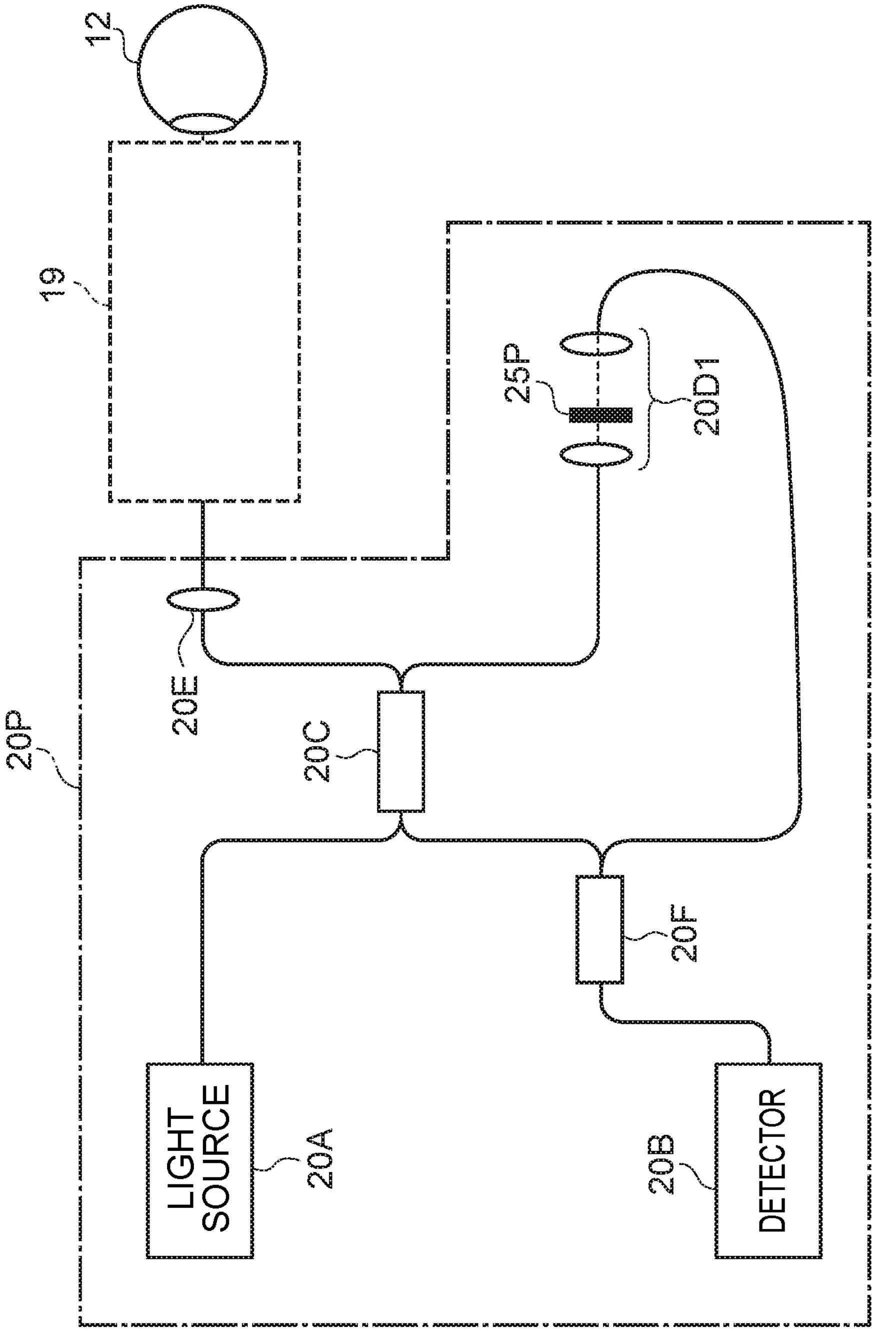
FIG. 3A is a block diagram illustrating a configuration of an electrical system of an OCT unit 20P.

As illustrated in FIG. 3A, the OCT unit 20P includes a light source 20A, a detector 20B, a first light coupler 20C, a reference optical system 20D1, a collimator lens 20E, and a second light coupler 20F, and executes OCT imaging of portions to be OCT imaged that have been specified as described later.

Figure 3B:
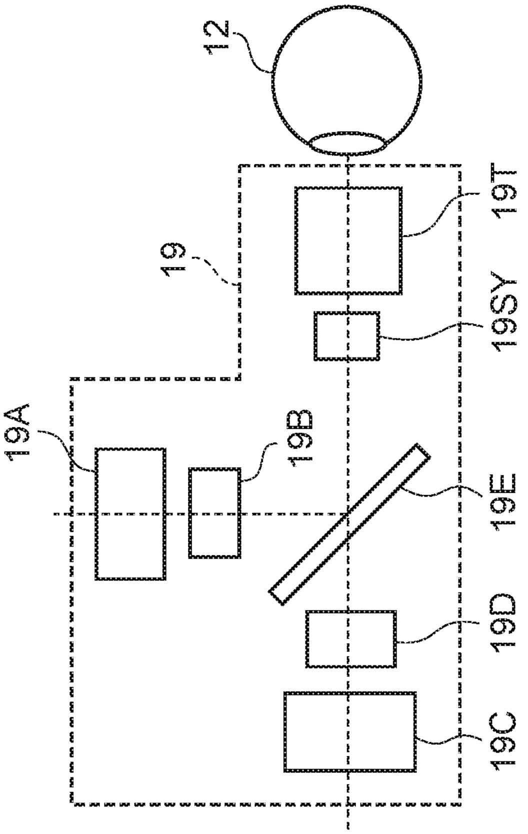
FIG. 3B is a diagram illustrating a configuration of an imaging optical system 19.

As illustrated in FIG. 3B, the imaging optical system 19 includes a focus mechanism 19A for use with the OCT unit 20P, a first scanner 19B for scanning light from the OCT unit 20P in the X direction, a focus mechanism 19C for use with the SLO unit 18, and a second scanner 19D for scanning light from the SLO unit 18 in the X direction. The imaging optical system 19 reflects light from the OCT unit 20P toward the eye to be examined 12 and reflects light that was reflected at the fundus of the eye to be examined 12 toward the OCT unit 20P, and includes a dichromic mirror 19E that transmits the light from the SLO unit 18 toward the eye to be examined 12 and transmits light reflected at the fundus of the eye to be examined 12 toward the SLO unit 18. The imaging optical system 19 also includes a common scanner 19SY that scans both light from the OCT unit 20P reflected by the dichromic mirror 19E and light from the SLO unit 18 transmitted through the dichromic mirror 19E, and an object lens 19T.

The object lens 19T is an example of an "object optical system" of technology disclosed herein.

The object lens 19T includes a non-illustrated bonded lens (stuck-together lens) formed by bonding plural lenses together using an adhesive. The first scanner 19B, the second scanner 19D, and the common scanner 19SY are optical elements capable of deflecting light beams. For example, a Galvano mirror or the like may be employed as the first scanner 19B and the common scanner 19SY. A polygon mirror or the like may be employed as the second scanner 19D.

As illustrated in FIG. 3A, the light source 20A of the OCT unit 20P emits light of plural different wavelengths. The light emitted from the light source 20A is split by the first light coupler 20C. One part of the split light serves as measurement light and is incident to the imaging optical system 19 after being formed into parallel light by the collimator lens 20E. The measurement light is adjusted in focus by the focus mechanism 19A, and is scanned respectively in the X direction and the Y direction by the first scanner 19B and the common scanner 19SY. The scanned light is illuminated through the pupil and onto the fundus.

The measurement light reflected by the fundus is incident to the OCT unit 20P via the imaging optical system 19, and is incident to the second light coupler 20F via the collimator lens 20E and the first light coupler 20C.

The other part of light that was emitted from the light source 20A and split at the first light coupler 20C serves as reference light incident to the reference optical system 20D1, and is incident to the second light coupler 20F through the reference optical system 20D1. The reference optical system 20D1 includes, as well as plural lenses, a dispersion generating section 25P that generates wavelength dispersion in the reference light. The dispersion generating section 25P serves as an example of a "dispersion section" of technology disclosed herein.

The dispersion generating section 25P is configured from a parallel plate glass of a medium and thickness determined so as to impart dispersion of a specific amount to the reference light. The wavelength dispersion generated in the reference light by the dispersion generating section 25P is a unique phenomenon according to the medium and thickness of the dispersion generating section 25P. Note that in the present exemplary embodiment the dispersion generating section 25P configured from the specific medium is formed on the light path of the reference light. The reference light transmitted through the dispersion generating section 25P is imparted with dispersion by the dispersion generating section 25P.

A degree of resolution lowering in a depth direction of a coherence signal changes according to the magnitude of dispersion of the dispersion generating section 25P. The greater the resolution lowering of the coherence signal, the more easily artifacts are discriminated, as described later. This means that, taking the resolution when dispersion is not imparted as a reference, preferably a dispersion that lowers resolution by 1 part in 2 parts or more parts is imparted to the reference light by the dispersion generating section 25P. However, if the dispersion of the dispersion generating section 25P is too great (for example, a dispersion lowering the resolution to 1 part in 100 parts) then this makes compensation by dispersion compensation difficult due to the resolution of the coherence signal being lowered too far.

The measurement light reflected at the eye to be examined and the reference light imparted with dispersion by the dispersion generating section 25P are both incident to the second light coupler 20F. The reference light and the measurement light interfere with each other at the second light coupler 20F to generate interference light. The interference light is photo-detected at the detector 20B. A coherence signal detected by the detector 20B is employed by the control device 16 to generate an OCT image.

The interference light obtained by the measurement light reflected at the eye to be examined interfering with the reference light imparted with the specific amount of dispersion is affected by the dispersion by the dispersion generating section 25P, lowering the resolution in the depth direction. However, self-coherent light (constructively interfering light) arising from an optical element such as the object lens 19T in the imaging optical system 19 interferes by interfered the measurement light, and so is not affected by the dispersion induced by the dispersion generating section 25P. In cases in which such self-coherent light has been generated, the light photo-detected by the detector 20B contains interference light obtained by the measurement light reflected at the eye to be examined interfering with the reference light imparted with the specific amount of dispersion, as well as self-coherent light due to the optical element such as the object lens 19T in the imaging optical system 19.

In the technology disclosed herein, artifacts arising from the self-coherent light (the constructively interfering light) due to the optical element in the imaging optical system 19 can be removed by combining the reference light imparted with dispersion by the dispersion generating section 25P with dispersion compensation of the coherence signal. Details regarding the method for removing the artifacts are described later.

The SLO unit 18 illustrated in FIG. 2 includes plural light sources, for example a light source of blue (B) light, a light source of green (G) light, a light source of red (R) light, and a light source of IR light (infrared rays (for example, near infrared light)), and includes plural optical systems to reflect or transmit light from these light sources and guide the light onto one light path toward the imaging optical system 19.

The light incident from the SLO unit 18 to the imaging optical system 19 is adjusted in focus by the focus mechanism 19C, and scanned in the X direction and the Y direction by the second scanner 19D and the common scanner 19SY, respectively. Scanning light passing through the pupil is illuminated onto a posterior eye portion of the eye to be examined 12. The reflected light that was reflected by the fundus passes through the imaging optical system 19 and is incident to the SLO unit 18.

The SLO unit 18 includes plural photodetector elements corresponding to the plural light sources listed above, and includes plural beam splitters to guide the reflected light of the light from each of these light source to the photodetector element corresponding to the respective light sources. An SLO image is generated by the control device 16 using the signals detected by each of the photodetector elements.

The eye axial length measurement device 120 illustrated in FIG. 1 measures an eye axial length that is a length along the eye axis direction of the eye to be examined 12. The measured eye axial length is transmitted to the server 140. The server 140 stores the eye axial lengths of patients in association with patient IDs.

The server 140 and the viewer 150 illustrated in FIG. 1 each are configured by a computer including a non-illustrated CPU, RAM, ROM, input/output (I/O) port, and the like. A storage device, display, mouse, keyboard, and communication interface (I/F) are connected to the input/output (I/O) port. Communication with other devices connected to the network 130 is possible through the communication interface (I/F).

Figure 4:
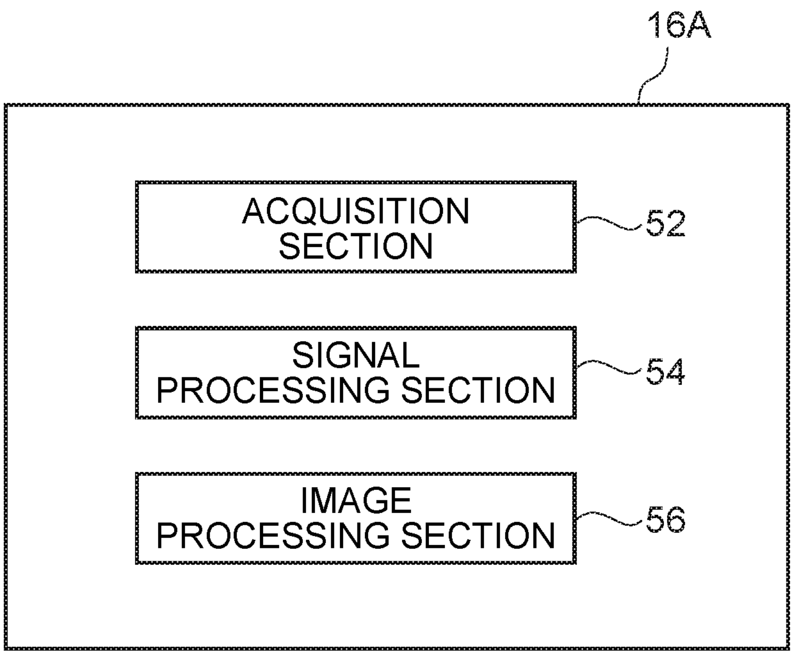
FIG. 4 is a functional block diagram of a CPU 16A of a control device 16.

Next, description follows regarding various functions implemented by a signal processing program executed by the CPU 16A of the control device 16, see FIG. 4. The signal processing program includes an acquisition function to acquire a coherence signal to be processed, a signal processing function for the acquired coherence signal, and an image processing function to generate an OCT image. The CPU 16A functions as an acquisition section 52, a signal processing section 54, and an image processing section 56, as illustrated in FIG. 4, by the CPU 16A executing a signal processing program including each function.

Figure 5A:
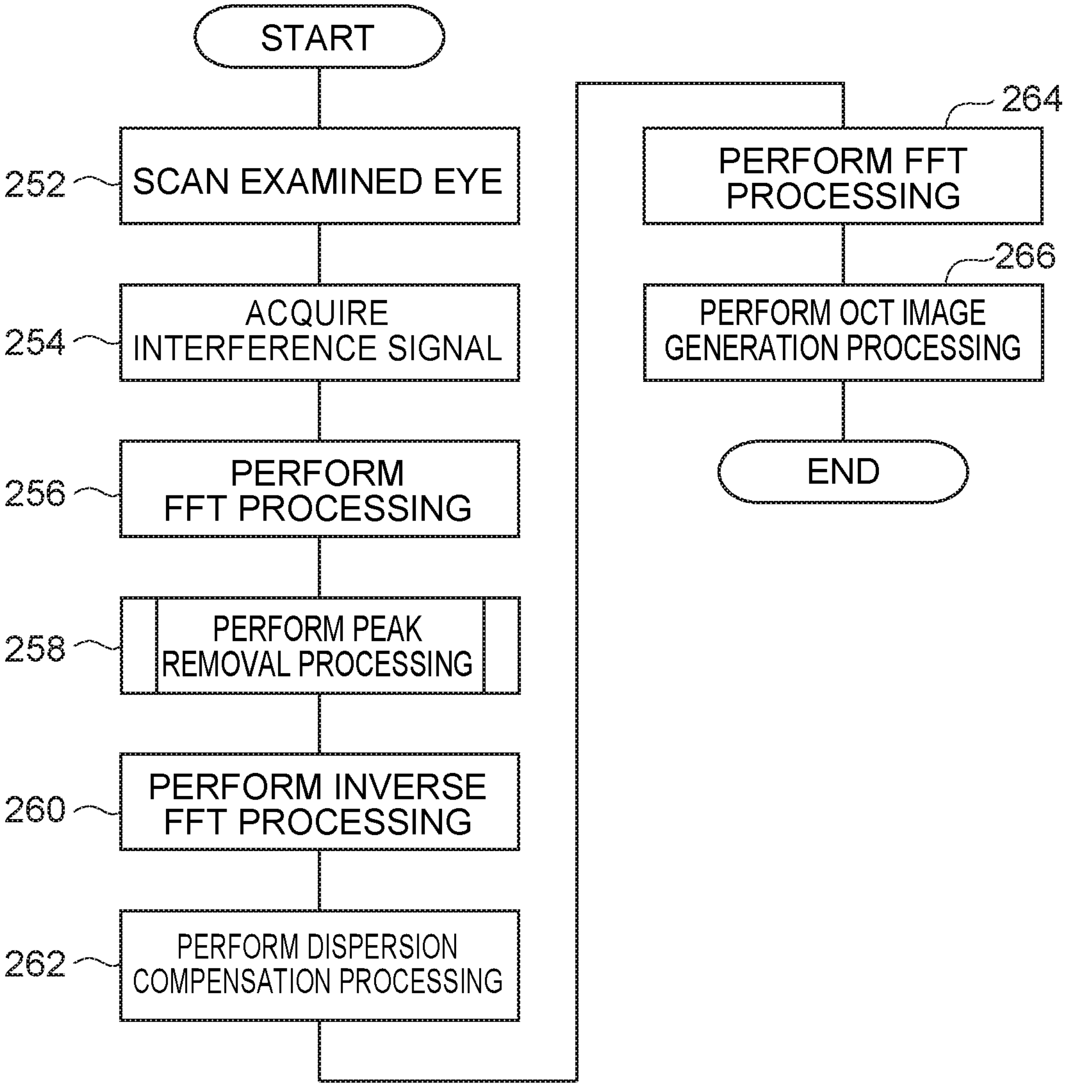
FIG. 5A is a flowchart illustrating processing by the control device 16.
Figure 5B:
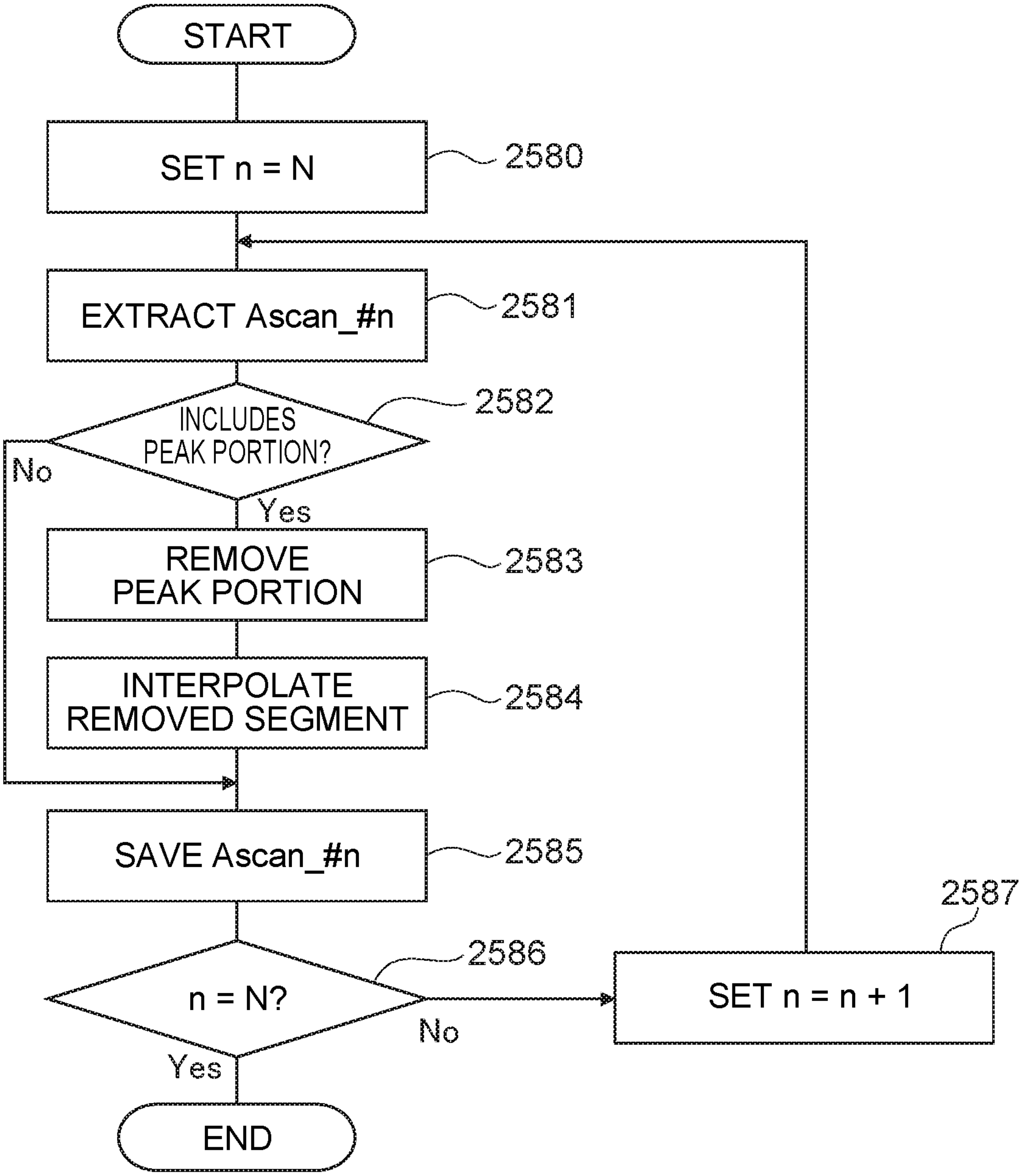
FIG. 5B is a flowchart illustrating details of peak removal processing at step 258 of FIG. 5A by the control device 16.

Next, detailed explanation follows regarding the signal processing by the control device 16, with reference to FIG. 5A and FIG. 5B. The signal processing illustrated in the flowcharts of FIG. 5A and FIG. 5B is implemented by the CPU 16A of the control device 16 executing the signal processing program. This signal processing starts when a portion of the fundus of the eye to be examined of the patient to be OCT imaged on the retina has been specified through the input/display device 16E and a non-illustrated start button displayed on the input/display device 16E has been pressed.

The acquisition section 52 scans the eye to be examined 12 at step 252 of FIG. 5A. More specifically, the acquisition section 52 controls the OCT unit 20P and the imaging optical system 19, and executes OCT imaging of the imaging position of the eye to be examined 12 specified by the user. A coherence signal CS obtained by OCT imaging is acquired by the acquisition section 52 at step 254. In cases in which the fundus of the eye to be examined 12 is the imaging position, the imaging optical system 19 is controlled such that the measurement light so that it converges on the fundus. The interference light obtained by the measurement light reflected at the fundus interfering with the reference light imparted with dispersion by the dispersion generating section 25P is photo-detected (detected) by the detector 20B. The detector 20B outputs the coherence signal CS (detection signal) to the control device 16 for storing in the RAM 16B. The acquisition section 52 acquires the coherence signal CS from the RAM 16B. As state above, in cases in which self-coherent light is generated by the optical element of the imaging optical system 19, this self-coherent light is also incident to the detector 20B along with the interference light obtained by the measurement light reflected at the fundus interfering with the reference light imparted with dispersion by the dispersion generating section 25P. Thus in such cases the interfering light based on the reflected light from the eye to be examined 12 and the self-coherent light based on the imaging optical system are contained in the coherence signal CS.

At step 256 the image processing section 56 acquires an OCT signal TS by executing fast Fourier transform (FFT) processing on the coherence signal CS.

At step 258, the image processing section 56 detects a peak portion that is a sharp signal portion in the OCT signal TS where there is a rapid change in brightness, and executes peak removal processing to remove this peak portion. This peak removal processing will now be explained in detail using FIG. 5B. The image processing section 56 generates a first corrected OCT signal TSA from which the peak portion has been removed.

At step 260, the image processing section 56 generates a first corrected coherence signal CSA (corrected detection signal from which noise is removed) by executing inverse fast Fourier transform processing (FFT processing) on the first corrected OCT signal TSA. Due to the dispersion being wavelength dispersion, the signal compensation should be performed in the frequency domain, and the first corrected coherence signal CSA is generated by performing inverse FFT processing on the first corrected OCT signal TSA.

At step 262, the image processing section 56 executes dispersion compensation processing. More specifically, the image processing section 56 compensates for the effect of dispersion from the first corrected coherence signal CSA imparted by the dispersion generating section 25P. A known dispersion compensation algorithm may be freely applied as this dispersion compensation processing. The image processing section 56 compensates for the effect of dispersion imparted by the dispersion generating section 25P by performing the dispersion compensation processing, and also generates a second corrected detection signal CSB from which artifacts have been removed.

At step 264, the image processing section 56 acquires the second corrected OCT signal TSB for which the effect of dispersion has been compensated and from which artifacts have been removed by executing FFT processing on the second corrected detection signal CSB for which the effect of dispersion imparted by the dispersion generating section 25P has been compensated and from which artifacts have been removed.

At step 266, the image processing section 56 generates an OCT image (tomographic image) of the eye to be examined 12 by performing eyeball shape compensation, full-range processing, and the like based on the second corrected OCT signal TSB. The image processing section 56 may also perform processing such as segmentation processing to make discrete layers, such as the retina, the cornea, and the like, of the obtained tomographic image visible, may also perform processing to calculate and find a layer thickness of each of the segmented layers, and may also perform processing to generate an en-face image. Note that the image processing section 56 may generate an en-face image from OCT volume data in cases in which the OCT signal is three-dimensional data (OCT volume data) obtained by a C scan.

At step 266, the image processing section 56 outputs the generated tomographic image and a second corrected OCT signal TSB to the RAM 16B or to non-illustrated external storage device. Signal processing (namely, execution of the signal processing program) ends when the processing of step 266 is finished.

In this manner, the peak portion caused by self-coherent light generated by the optical element of the imaging optical system 19 is removed from the OCT signal, the first corrected OCT signal from which the peak portion has been removed is generated, inverse Fourier transformation is performed on this first corrected OCT signal to generate a corrected detection signal, a corrected coherence signal resulting from performing dispersion compensation on the corrected detection signal is generated, and Fourier transformation is performed on the corrected coherence signal so as to obtain the second corrected OCT signal. This thereby enables an OCT image (tomographic image) to be obtained in which artifacts have been suppressed.

Next, detailed explanation follows regarding peak removal processing of step 258 of FIG. 5A, with reference to the flowchart of FIG. 5B.

At step 2580, the image processing section 56 sets a parameter n to 1. The parameter n is a value from 1 to N, wherein N is the number of A-SCANs configuring the OCT signal TS. N is an integer of 1 or greater.

Next, at step 2581, the image processing section 56 extracts a signal ASn_#n of an $n^{th}$ A-SCAN from the OCT signal TS.

Figure 7A:
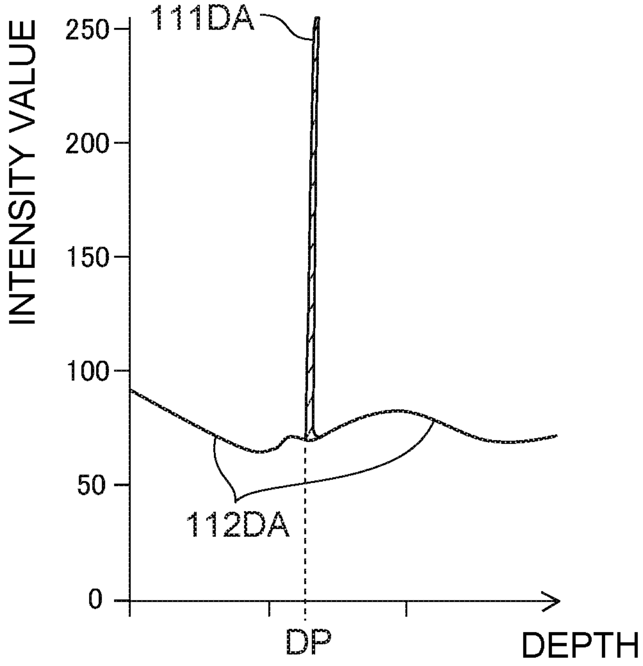
FIG. 7A is a diagram illustrating an OCT signal when reference light is not transmitted through a diffusion generation section 25P.

At step 2582, the image processing section 56 determines whether or not there is a peak portion present in the signal ASn. The peak portion contained in the signal ASn is, for example as illustrated in FIG. 7A, a characteristic peak portion 111DA where there is a rapid change in intensity value of the signal ASn. The characteristic peak portion 111DA is, for example, a portion where a width at half intensity value is smaller than a specific value, more specifically a portion where, for example, a full width at half maximum (FWHM) is smaller than, for example, 8 μm. In such cases the image processing section 56 determines from the signal ASn whether or not there is a portion present where the full width at half maximum is smaller than 8 μm in the signal ASn. Alternatively various known peak detection method may be employed.

FIG. 7A is a diagram illustrating a waveform of a signal ASn of an A-SCAN in which the peak portion 111DA is present, with intensity values of the signal ASn indicated on the vertical axis and depth indicated on the horizontal axis. The peak portion 111DA is positioned at a position of depth DP on the horizontal axis. The peak portion 111DA is where self-coherent light is present in the measurement light due to an optical element in the imaging optical system 19, and is an intensity value of a detection signal arising from self-coherent light not affected by dispersion. The signal portions 112DA of FIG. 7A are intensity values of the detection signal of interference light obtained when the measurement light reflected at the eye to be examined 12 interferes with the reference light imparted with dispersion by the dispersion generating section 25P. The signal portions 112DA have a resolution in the depth direction significantly lowered due to the effect of dispersion.

Figure 6:
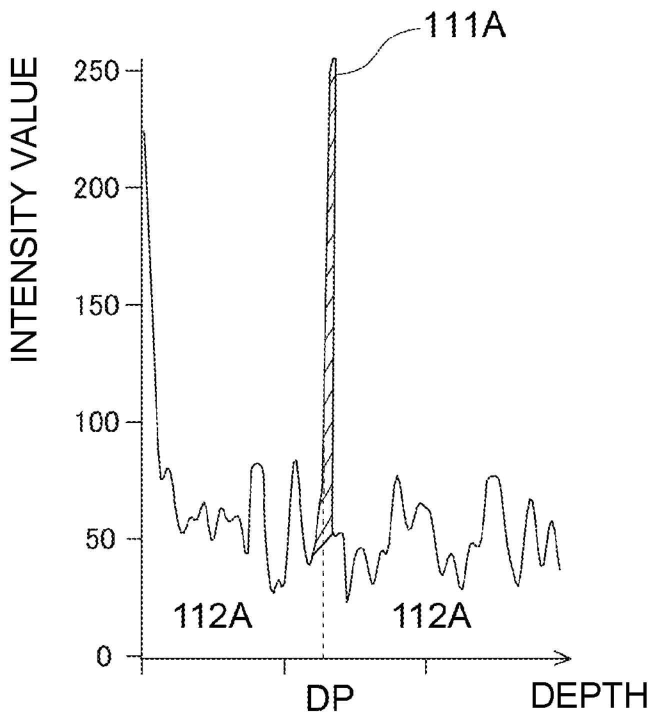
FIG. 6 is diagram illustrating an OCT signal when reference light is not transmitted through a diffusion generation section 25P.

The signal ASn when there is no dispersion generating section 25P present on the reference light pathway contains, as illustrated in FIG. 6, portions 112A of intensity values of detection signal due to interference light obtained by the measurement light reflected at the eye to be examined 12 interfering with the reference light not imparted with dispersion, and includes intensity values of detection signal due to self-coherent light in the measurement light arising from the optical element in the imaging optical system 19, namely includes a peak portion 111A. The peak portion 111A is positioned at a depth DP that is the same position on the horizontal axis as that of the peak portion 111DA of FIG. 7A. This means that a difference between the conditions of the signals ASn illustrated in FIG. 7A and FIG. 6 is merely whether or not the dispersion generating section 25P is provided on the reference light pathway in the reference optical system 20D1, and the same conditions apply for the measurement light passing along the measurement light path.

Suppose that there was an intensity value corresponding to a structural object of the eye to be examined 12 at the position of depth DP on the horizontal axis, the OCT signal would be blurred due to being imparted with dispersion thereby, and intensity values of the detection signal due to self-coherent light of the measurement light arising from the optical element in the imaging optical system 19 would be clearly distinguishable. Namely, arranging the dispersion generating section 25P on the reference light pathway and imparting a specific dispersion to the reference light enables distinguishing between the intensity values in the OCT signal corresponding to a structural object of the eye to be examined 12 at the position of depth DP on the horizontal axis, and the intensity values due to the self-coherent light of the measurement light due to the optical element in the imaging optical system 19.

Such a peak portion is noise in the OCT signal of the eye to be examined 12. This is a cause of a hitherto unwanted image (hereafter referred to as an artifact) that does not correspond to a structure of the eye to be examined 12 and is caused by self-coherent light arising from the object lens 19T or another optical element or the like of the imaging optical system 19 of the ophthalmic device 110.

The reason such a sharp peak portion is contained as noise in such a signal ASn is as follows. The object lens 19T includes a bonded lens formed by adhering plural lenses together using an adhesive. When the measurement light is incident to the object lens 19T, not only is the measurement light transmitted through the plural lenses, but the measurement light is also reflected at lens surfaces of the plural lenses in the bonded lens. The measurement light reflected at the lens surfaces results in self-coherence (an etalon) between the reflected light and the measurement light. Noise is contained in the measurement light due to this self-coherence. Note that more noise arises when the eye to be examined 12 is near-sighted than when far-sighted, and larger artifacts are generated in the tomographic images.

Moreover, when the presence of an artifact caused by an optical element such as the object lens 19T of the imaging optical system 19 in the ophthalmic device 110 is already known, then the depth DP on the horizontal axis is pre-identified for the peak portion 111A in the OCT signal. This means that in cases in which an artifact caused by an optical element of the imaging optical system 19 such as the object lens 19T is known to be present, then having a look up table indicating the relationship between the imaging position of the eye to be examined 12 and the depth DP on the horizontal axis of the peak portion 111A means that the determination of step 2582 is no longer needed. Whether or not this is an A scan in which there is a peak portion 111A present is known from referencing such a look up table at step 2583, and the depth DP on the horizontal axis is determined when this is an A scan in which there is a peak portion 111A present, enabling the intensity value of the depth DP to be removed.

Processing proceeds to step 2585 in cases in which determination by the image processing section 56 at step 2582 is that is no sharp peak portion present in the signal ASn (step 2582: NO). At step 2585, the image processing section 56 saves the signal ASn as the $n^{th}$ A-SCAN signal in a RAM 16B.

Figure 7B:
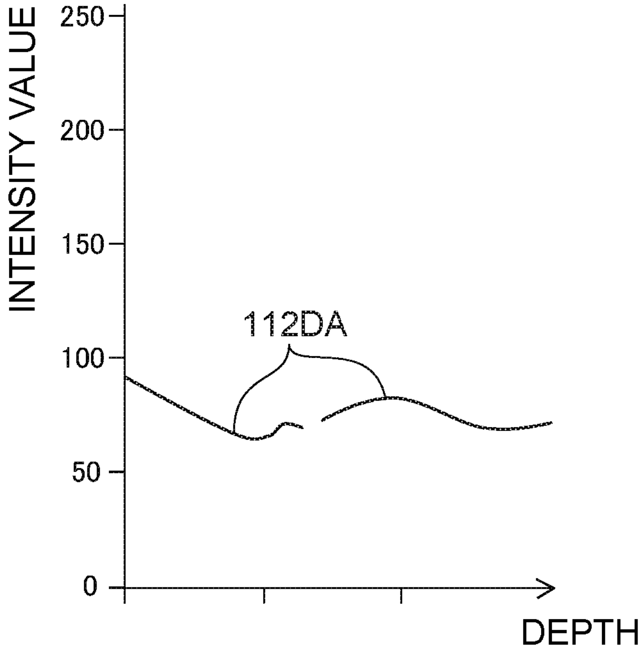
FIG. 7B is a diagram illustrating a signal when a peak portion has been removed from an OCT signal in a case in which reference light has been transmitted through the diffusion generation section 25P.

Processing proceeds to step 2582 in cases in which determination at step 2582 is that there is a sharp peak portion present in the signal ASn (step 2584: YES). Then at step 2583, the image processing section 56 sets the intensity value to zero for the range of the peak portion 111DA as illustrated in FIG. 7B. The image processing section 56 then removes the peak portion 111DA from the signal ASn.

Instead of making the intensity value of the peak portion 111DA zero, the intensity value may be decreased to an average value so as to be the average value of the intensity value at the periphery of the peak portion.

The peak portion 111DA is the intensity values of the detection signal arising from self-coherent light of the measurement light due to the optical element in the imaging optical system 19, and so is blurred by dispersion even though removed from the signal ASn, enabling the effect on the intensity value corresponding to a structural object of the eye to be examined 12 to be ignored.

Figure 7C:
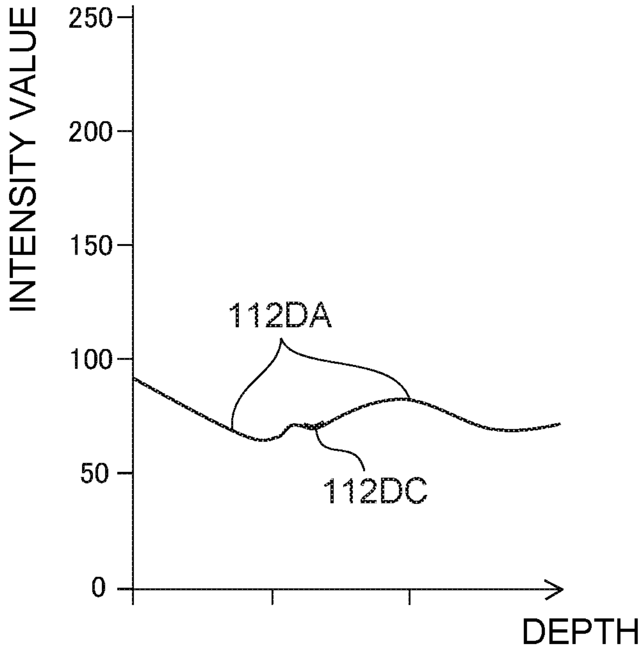
FIG. 7C is a diagram illustrating a signal when reference light has been transmitted through the diffusion generation section 25P for a case in which a peak portion has been removed from an OCT signal and interpolation has been performed on a removal range.

Next, at step 2584, the image processing section 56 performs processing to interpolate intensity values 111DC in a range where the peak portion 111DA was present, and as illustrated in FIG. 7C, generates a signal CASn in which the removed peak portion has been interpolated. The image processing section 56 takes the signal CASn as a corrected $n^{th}$ A-SCAN signal.

Any known interpolation method, such as interpolation using linear interpolation, spline interpolation, or Gaussian process regression, may be employed as the interpolation processing, enabling intensity values 111DC to be derived for a range where the peak portion 111DA was present based on the intensity value of the signal portions 112DA at the periphery of the peak portion 111DA.

Then at step 2585, the image processing section 56 saves the signal CASn as the $n^{th}$ A-SCAN signal in the RAM 64.

Next the image processing section 56 determines whether or not n equals N at step 2586, and processing proceeds to step 2587 unless n equals N (step 2586: NO). At step 2587, the image processing section 56 sets n=n+1 before repeating the processing of steps 2581 to 2585.

However if n equals N (step 2586: YES), the peak removal processing is finished for all of the N individual A-SCANs configuring the OCT signal TS, the corrected OCT signal TSA is obtained therefrom and the flowchart of FIG. 5B is ended. Step 260 of FIG. 5A is then started.

In the present exemplary embodiment as described above, an OCT signal is obtained from the interference light resulting from the measurement light reflected at the eye to be examined interfering with the reference light imparted with dispersion by the dispersion generating section 25P, enabling effective removal of noise in the A-SCAN signal due to self-coherence of measurement light due to an optical element such as the object lens 19T or the like of the imaging optical system 19 in the ophthalmic device 110. The OCT signal resulting from removing the noise due to self-coherence of measurement light from the A-SCAN signal is subjected to inverse Fourier transformation so as to obtain a corrected coherence signal. The effect of dispersion imparted by the dispersion generating section 25P is compensated by performing dispersion compensation on this corrected coherence signal. The corrected coherence signal on which dispersion compensation has been performed is then subjected again to Fourier transformation so as to enable an OCT signal to be obtained from which artifacts have been removed.

Next, description follows regarding modified examples of the technology disclosed herein. Note that the same reference numerals will be appended to similar portions to those of the exemplary embodiment described above and detailed explanation thereof will be omitted, with description focusing on portions that differ.

In the exemplary embodiment described above, the reference optical system 20D1 of the OCT unit 20P includes the dispersion generating section 25P. The exemplary embodiment illustrated in FIG. 3A includes the dispersion generating section 25P configured from parallel plate glass, however the technology disclosed herein is not limited thereto.

Figure 8:
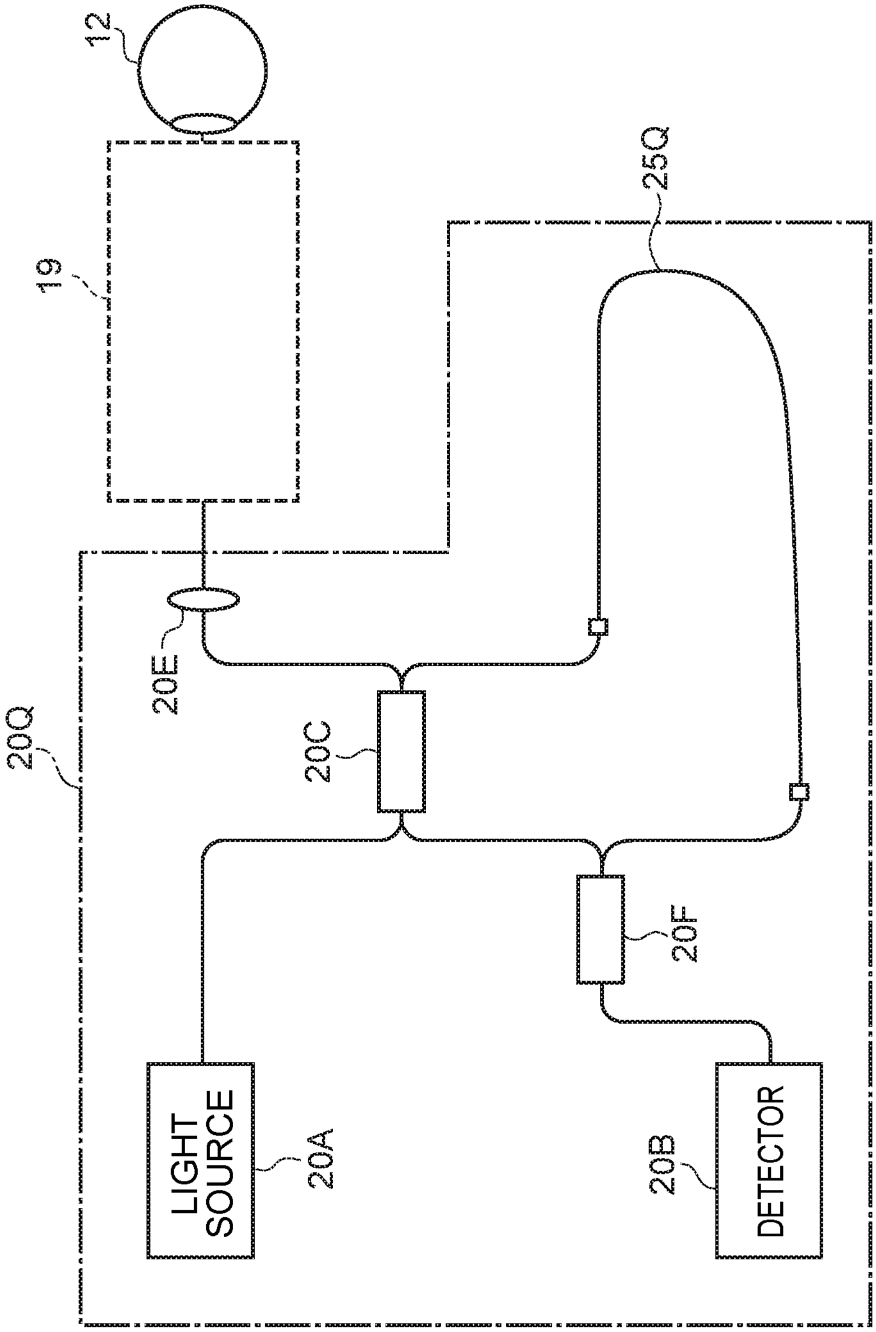
FIG. 8 is a block diagram illustrating a configuration of an electrical system of an OCT unit 200 of a first modified example.

FIG. 8 illustrates a configuration of an electrical system of the imaging optical system 19 and the OCT unit 20Q of a first modified example. As illustrated in FIG. 8, a fiber 25Q of length determined so as to impart the above dispersion to the reference light may be employed as the dispersion generating section instead of the reference optical system 20D1 illustrated in FIG. 3A. The fiber 25Q is arranged on the light path of the reference light.

Figure 9:
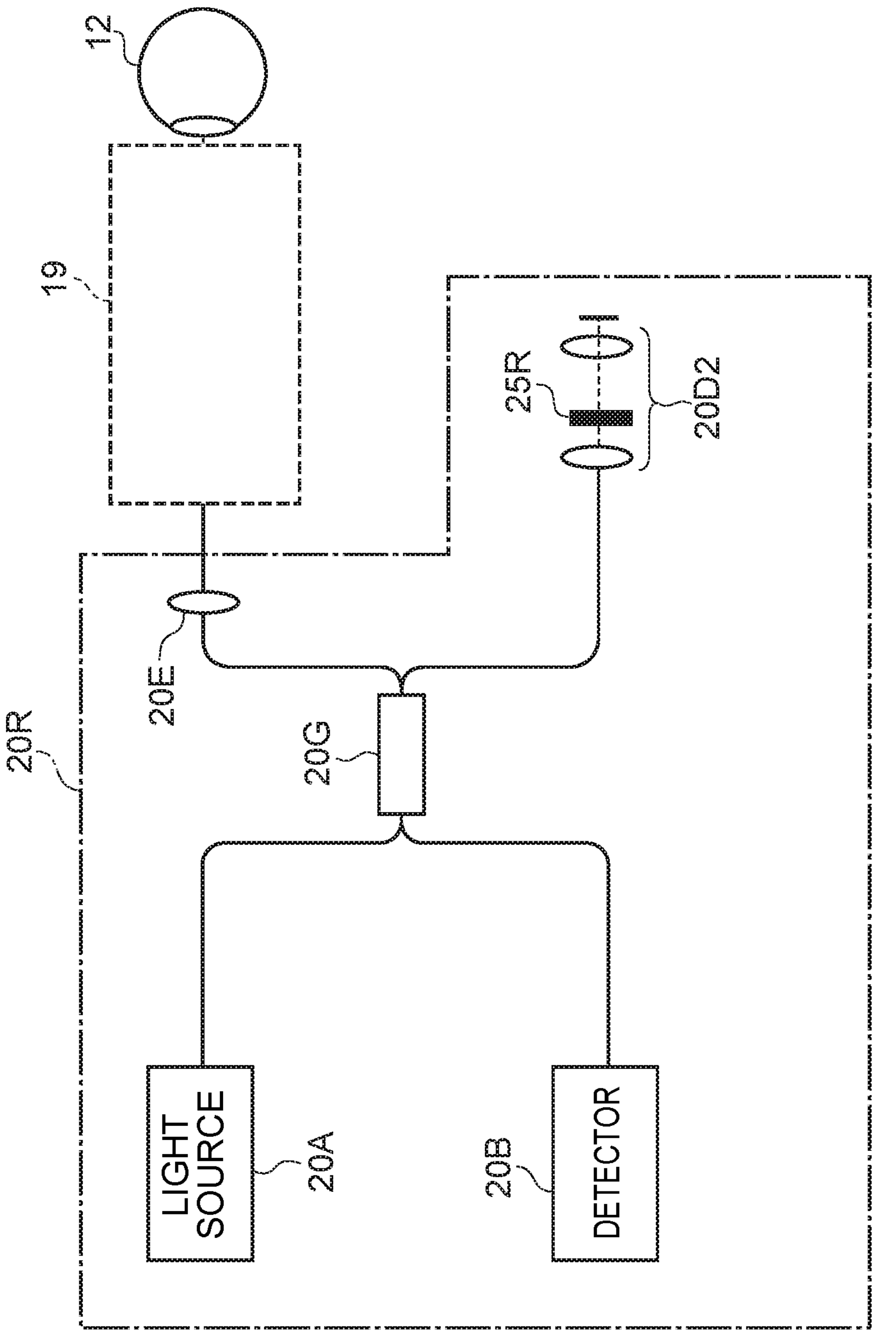
FIG. 9 is a block diagram illustrating a configuration of an electrical system of an OCT unit 20R of a second modified example.

A configuration of an electrical system of the imaging optical system 19 and the OCT unit 20R of a second modified example is illustrated in FIG. 9. As illustrated in FIG. 9, a light coupler 20G may be provided instead of the first light coupler 20C and the second light coupler 20F illustrated in FIG. 3A, and a reference optical system 20D2 including plural lenses, a dispersion generating section 25R, and a reflection mirror may be employed instead of the reference optical system 20D1 illustrated in FIG. 3A. The light emitted from the light source 20A is split at the light coupler 20G. One part of the split light serves as measurement light. The measurement light reflected by the fundus is incident through the imaging optical system 19 to the OCT unit 20R and is incident to the light coupler 20G. The other part of the light emitted from the light source 20A and split by the light coupler 20G serves as the reference light, is incident to the reference optical system 20D2, is transmitted through the plural lenses and the dispersion generating section 25R, is reflected by the reflection mirror, is transmitted through the plural lenses and the dispersion generating section 25R, and is incident to the light coupler 20G. The dispersion generating section 25R is a parallel plate glass of a medium and thickness determined so as to impart the above dispersion to the reference light. This light incident to the light coupler 20G, namely the measurement light reflected at the fundus and the reference light interfere at the light coupler 20G and generate interference light. The interference light is photo-detected at the detector 20B.

The dispersion generating section 25R is arranged on the light path of the reference light.

Moreover, in the exemplary embodiment described above the dispersion generating section is arranged on the light path of the reference light and imparts dispersion to the reference light. However the technology disclosed herein is not limited thereto. A configuration may be adopted in which dispersion is imparted only to the measurement light instead of to the reference light by arranging the dispersion generating section only on the light path of the measurement light, or a configuration may be adopted in which dispersion is imparted to the measurement light as well as to the reference light by arranging a dispersion generating section on both the light path of the reference light and the light path of the measurement light.

Figure 10:
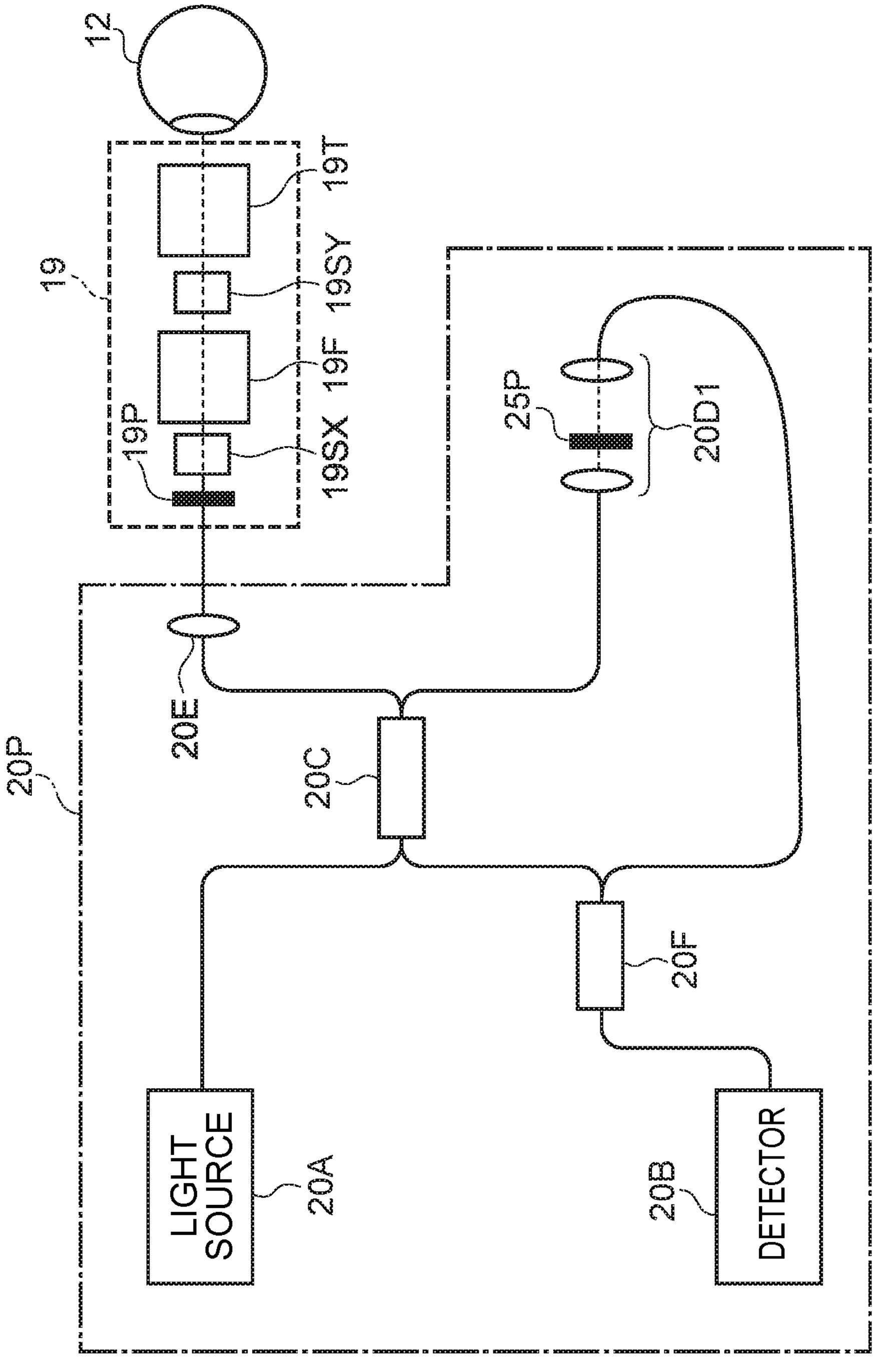
FIG. 10 is a block diagram illustrating a configuration of an electrical system of an OCT unit 20P of a third modified example.

FIG. 10 illustrates a configuration of an electrical system of an imaging optical system 19 and an OCT unit 20P of a third modified example. FIG. 10 illustrates an example in which dispersion is imparted to the measurement light as well as to the reference light. As illustrated in FIG. 10, the OCT unit 20P as well as including the reference optical system 20D1 illustrated in FIG. 3A also includes a dispersion generating section 19P provided to the imaging optical system 19 so as to transmit the measurement light. Dispersions having mutually different dispersion properties are imparted by the dispersion generating section 25P and the dispersion generating section 19P to the reference light and the measurement light on each of the light paths. The dispersion generating section 25P and the dispersion generating section 19P are each a parallel plate glass having a medium and thickness determined so as to impart the above dispersion to the reference light and the measurement light. Note that the example illustrated in FIG. 8 may also be configured including the dispersion generating section 19P provided to the imaging optical system 19 so as to transmit the measurement light. The third modified example is also able to distinguish between intensity values in the OCT signal corresponding to a structural object of the eye to be examined and intensity values in the OCT signal due to self-coherent light of the measurement light arising from an optical element in the imaging optical system.

As described above, the exemplary embodiments of technology disclosed herein remove noise in the OCT signal arising from self-coherence of the measurement light generated in the object optical system and so a tomographic image can be obtained in which artifacts have been suppressed.

Although a case has been described in the exemplary embodiment described above in which a bonded lens is provided to the object lens 19T as at least one optical system that generates an artifact in the tomographic images in which the above self-coherence arises, the technology disclosed herein is not limited thereto.

For example, firstly a configuration may be adopted in which plural (for example two) lenses are provided in the object lens 19T disposed in close proximity to each other on each side of an extremely thin layer of air of specific thickness. Each of the plural lenses in such cases are arranged with surfaces of substantially the same curvature (radius of curvature surfaces) in close proximity to each other.

Secondly, a configuration may be adopted in which plural (for example two) lenses are placed in contact with each other without adhesive in the object lens 19T. The plural lenses in such cases make contact with surfaces of the same curvature (radius of curvature surfaces), and configure an optically contacted lens group.

Thirdly, a configuration may be adopted in which plural (for example two) convex lenses are provided arranged in close proximity to each other in the object lens 19T. The plural lenses in such cases have apexes that do not contact each other.

Fourthly, a configuration may be adopted in which plural (for example two) convex lenses are provided with apexes that contact each other in the object lens 19T. The plural lenses in such cases contact each other at their apexes.

Fifthly, a configuration may be adopted in which a parallel plate glass is provided to the object lens 19T.

Although in each of the examples described above cases have been described in which at least one optical system that generates an artifact in tomographic images due to self-coherence arising has been provided to the object lens 19T, the technology disclosed herein is not limited thereto. The technology disclosed herein is applicable to cases in which, for example, at least one optical system that generates an artifact in tomographic images due to self-coherence arising is present in the focus mechanisms 19A, 19C of the imaging optical system 19 on the optical path from the eye to be examined 12 to the detector 20B and/or on the optical path from the eye to be examined 12 to the detector 20B in the OCT unit 20P.

In the present disclosure, each of the configuration elements (devices and the like) may be present singly or present as two or more thereof as long as inconsistencies do not result therefrom.

Although explanation has been given in the exemplary embodiments described above regarding an example in which a computer is employed to implement image processing using a software configuration, the technology disclosed herein is not limited thereto. For example, instead of a software configuration employing a computer, the image processing may be executed solely by a hardware configuration such as a field programmable gate array (FPGA) or an application specific integrated circuit (ASIC). Alternatively, a configuration may be adopted in which some processing out of the image processing is executed by a software configuration, and the remaining processing is executed by a hardware configuration.

It must be understood that each signal processing described above is merely an example thereof. Obviously redundant steps may be omitted, new steps may be added, and the processing sequence may be swapped around within a range not departing from the spirit of technology disclosed herein.

All publications, patent applications and technical standards mentioned in the present specification are incorporated by reference in the present specification to the same extent as if each individual publication, patent application, or technical standard was specifically and individually indicated to be incorporated by reference.

The invention claimed is:

1. An OCT signal processing method of a processor performing processing on a detection signal obtained by separating light emitted from a light source into measurement light and reference light, guiding the measurement light to an eye to be examined using an object optical system, guiding the reference light to a reference optical system, followed by photo-detecting interference light resulting from measurement light reflected from the eye to be examined interfering with the reference light, wherein dispersion is imparted to the reference light by a dispersion section provided to the reference optical system such that a difference in dispersion characteristics between the reference light and the measurement light is increased, the processing comprising:

- generating an OCT signal by performing Fourier transformation on the detection signal;
- detecting a peak portion in the OCT signal;
- generating a first corrected OCT signal by removing the peak portion from the OCT signal;
- generating a first corrected detection signal by performing inverse Fourier transformation on the first corrected OCT signal;
- compensating the dispersion contained in the first corrected detection signal and outputting a second corrected detection signal; and
- generating a second corrected OCT signal in which the dispersion has been compensated by performing Fourier transformation on the second corrected detection signal.

2. The OCT signal processing method of claim 1, further comprising a step of generating a tomographic image based on the second corrected OCT signal.

3. The OCT signal processing method of claim 1, wherein the peak portion is a portion having a width at half intensity value smaller than a specific value.

4. The OCT signal processing method of claim 1, wherein the peak portion arises due to constructively interfering light generated by the object optical system.

5. An ophthalmic device comprising a processor, wherein:

- the processor performs processing on a detection signal obtained by separating light emitted from a light source into measurement light and reference light, guiding the measurement light to an eye to be examined using an object optical system, guiding the reference light to a reference optical system, followed by photo-detecting interference light resulting from measurement light reflected from the eye to be examined interfering with the reference light;
- dispersion is imparted to the reference light by a dispersion section provided to the reference optical system such that a difference in dispersion characteristics between the reference light and the measurement light is increased; and
- the processor executes:
  - generating an OCT signal by performing Fourier transformation on the detection signal;
  - detecting a peak portion in the OCT signal;
  - generating a first corrected OCT signal by removing the peak portion from the OCT signal;
  - generating a first corrected detection signal by performing inverse Fourier transformation on the first corrected OCT signal;
  - compensating the dispersion contained in the first corrected detection signal and outputting a second corrected detection signal; and
  - generating a second corrected OCT signal in which the dispersion has been compensated by performing Fourier transformation on the second corrected detection signal.

6. The ophthalmic device of claim 5, wherein the processing further comprising:

- generating a tomographic image based on the second corrected OCT signal.

7. A non-transitory computer-readable medium storing a program that causes a computer to execute processing on a detection signal obtained by separating light emitted from a light source into measurement light and reference light, guiding the measurement light to an eye to be examined using an object optical system, guiding the reference light to a reference optical system, followed by photo-detecting interference light resulting from measurement light reflected from the eye to be examined interfering with the reference light, wherein dispersion is imparted to the reference light by a dispersion section provided to the reference optical system such that a difference in dispersion characteristics between the reference light and the measurement light is increased, the program causing the computer to execute:

generating an OCT signal by performing Fourier transformation on the detection signal;

detecting a peak portion in the OCT signal;

generating a first corrected OCT signal by removing the peak portion from the OCT signal;

generating a first corrected detection signal by performing inverse Fourier transformation on the first corrected OCT signal;

compensating the dispersion contained in the first corrected detection signal and outputting a second corrected detection signal; and generating a second corrected OCT signal in which the dispersion has been compensated by performing Fourier transformation on the second corrected detection signal.

8. The program of claim 7, wherein the program causes the computer to further execute a step of generating a tomographic image based on the second corrected OCT signal.

9. The OCT signal processing method of claim 2, wherein the peak portion is a portion having a width at half intensity value smaller than a specific value.

10. The OCT signal processing method of claim 2, wherein the peak portion arises due to constructively interfering light generated by the object optical system.

11. The OCT signal processing method of claim 3, wherein the peak portion arises due to constructively interfering light generated by the object optical system.

* * * * *